United States Patent
Hall et al.

(10) Patent No.: US 11,486,124 B2
(45) Date of Patent: Nov. 1, 2022

(54) TOILET WITH WASTE LOCATION DETECTION AND REMOVAL

(71) Applicant: Medic, Inc., Provo, UT (US)

(72) Inventors: David R. Hall, Provo, UT (US); David Crismon, Herriman, UT (US); Joshua Larsen, Spanish Fork, UT (US); Jared Reynolds, Spanish Fork, UT (US)

(73) Assignee: Hall Labs LLC, Provo, UT (US)

( * ) Notice: Subject to any disclaimer, the term of this patent is extended or adjusted under 35 U.S.C. 154(b) by 83 days.

(21) Appl. No.: 16/903,124

(22) Filed: Jun. 16, 2020

(65) Prior Publication Data

US 2020/0399880 A1 Dec. 24, 2020

Related U.S. Application Data

(60) Provisional application No. 62/888,670, filed on Aug. 19, 2019, provisional application No. 62/888,676, filed on Aug. 19, 2019, provisional application No. 62/862,579, filed on Jun. 17, 2019.

(51) Int. Cl.
| | |
|---|---|
| *E03D 5/01* | (2006.01) |
| *E03D 9/00* | (2006.01) |
| *G01N 33/483* | (2006.01) |
| *G01N 33/493* | (2006.01) |

(52) U.S. Cl.
CPC .............. *E03D 5/01* (2013.01); *E03D 9/00* (2013.01); *G01N 33/4833* (2013.01); *G01N 33/493* (2013.01)

(58) Field of Classification Search
CPC ............... E03D 9/08; E03D 5/01; E03D 9/10
USPC .......................................................... 4/432
See application file for complete search history.

(56) References Cited

U.S. PATENT DOCUMENTS

| | | | | |
|---|---|---|---|---|
| 3,815,158 | A * | 6/1974 | Schnyder | A47K 13/10 4/420 |
| 5,184,359 | A * | 2/1993 | Tsukamura | A61B 5/02241 4/314 |
| 5,241,712 | A * | 9/1993 | Mahoney | E03D 9/08 4/420.2 |
| 9,428,898 | B1 * | 8/2016 | Clements | E03D 9/08 |
| 2015/0082528 | A1 * | 3/2015 | Ding | E03D 5/01 4/321 |

(Continued)

FOREIGN PATENT DOCUMENTS

CN 107700619 A * 2/2018

OTHER PUBLICATIONS

CN 107700619A English machine translation printed Dec. 3, 2021 (Year: 2021).*

*Primary Examiner* — Christine J Skubinna (57) ABSTRACT

An analytical toilet is disclosed. The toilet is equipped to use energized flush water to clean excreta and other waste from the toilet. The toilet includes a bowl for receiving excreta from a user; at least one analytical device by which a sample of excreta is analyzed; a supply of flush water to be used to remove waste from a surface the of the toilet; an energizer to add energy to at least a portion of the to create energized flush water prior to its use in removing waste; and an orifice for directing a first jet of the energized flush water at the waste on the surface of the toilet. The disclosure also includes features to detect the location of waste in the toilet and selectively activate the energized flush water in order to clean the detected waste.

19 Claims, 9 Drawing Sheets

(56) References Cited

U.S. PATENT DOCUMENTS

| | | | |
|---|---|---|---|
| 2016/0000378 A1* | 1/2016 | Hall | A61B 5/14532 |
| | | | 702/19 |
| 2018/0002911 A1* | 1/2018 | Hall | E03D 5/105 |
| 2018/0030710 A1* | 2/2018 | Hall | E03D 9/10 |
| 2018/0184906 A1* | 7/2018 | Prokopp | A61B 5/0022 |
| 2020/0109545 A1* | 4/2020 | Ben Amram | A46B 15/0095 |

* cited by examiner

TOILET WITH WASTE LOCATION DETECTION AND REMOVAL

CROSS-REFERENCE TO RELATED APPLICATIONS

This application claims priority to U.S. Provisional Patent Application Nos. 62/862,579 titled "Toilet Using Pressurized Water for Washing Bowl" filed on 17 Jun. 2019, 62/888,670 titled "Toilet with High Pressure Flush Mechanism" filed on 19 Aug. 2019, 62/888,676 titled "Toilet with Hot Water Flush" filed on 19 Aug. 2019, each of which are incorporated herein by reference in their entirety.

TECHNICAL FIELD

The present disclosure relates to analytical toilets. More particularly, it relates to analytical toilets equipped to provide health and wellness information to the user.

BACKGROUND

The ability to track an individual's health and wellness is currently limited due to the lack of available data related to personal health. Many diagnostic tools are based on examination and testing of excreta, but the high cost of frequent doctor's visits and/or scans make these options available only on a very limited and infrequent basis. Thus, they are not widely available to people interested in tracking their own personal wellbeing.

Toilets present a fertile environment for locating a variety of useful sensors to detect, analyze, and track trends for multiple health conditions. Locating sensors in such a location allows for passive observation and tracking on a regular basis of daily visits without the necessity of visiting a medical clinic for collection of samples and data. Monitoring trends over time of health conditions supports continual wellness monitoring and maintenance rather than waiting for symptoms to appear and become severe enough to motivate a person to seek care. At that point, preventative care may be eliminated as an option leaving only more intrusive and potentially less effective curative treatments. An ounce of prevention is worth a pound of cure.

Just a few examples of smart toilets and other bathroom devices can be seen in the following U.S. Patents and Published Applications: U.S. Pat. No. 9,867,513, entitled "Medical Toilet With User Authentication"; U.S. Pat. No. 10,123,784, entitled "In Situ Specimen Collection Receptacle In A Toilet And Being In Communication With A Spectral Analyzer"; U.S. Pat. No. 10,273,674, entitled "Toilet Bowl For Separating Fecal Matter And Urine For Collection And Analysis"; US 2016/0000378, entitled "Human Health Property Monitoring System"; US 2018/0020984, entitled "Method Of Monitoring Health While Using A Toilet"; US 2018/0055488, entitled "Toilet Volatile Organic Compound Analysis System For Urine"; US 2018/0078191, entitled "Medical Toilet For Collecting And Analyzing Multiple Metrics"; US 2018/0140284, entitled "Medical Toilet With User Customized Health Metric Validation System"; and US 2018/0165417, entitled "Bathroom Telemedicine Station." The disclosures of all these patents and applications are incorporated by reference in their entireties.

SUMMARY

In a first aspect, the disclosure provides an analytical toilet equipped to use energized flush water to clean excreta and other waste from the toilet. The toilet includes a bowl for receiving excreta from a user; at least one analytical device by which a sample of excreta is analyzed; a supply of flush water to be used to remove waste from a surface the of the toilet; an energizer to add energy to at least a portion of the to create energized flush water prior to its use in removing waste; and an orifice for directing a first jet of the energized flush water at the waste on the surface of the toilet.

In a second aspect, the disclosure provides features to detect the location of waste in the toilet and selectively activating jets of the energized flush water in order to clean the detected waste.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, "toilet" is meant to refer to any device or system for receiving human excreta, including urinals.

As used herein, the term "bowl" refers to the portion of a toilet that is designed to receive excreta.

As used herein, the term "base" refers to the portion of the toilet below and around the bowl supporting it.

As used herein, the term "user" refers to any individual who interacts with the toilet and deposits excreta therein.

As used herein, the term "excreta" refers to any substance released from the body of a user including urine, feces, menstrual discharge, saliva, expectorate, and anything contained or excreted therewith.

As used herein, the term "manifold" is intended to have a relatively broad meaning, referring to a device with multiple conduits and valves to controllably distribute fluids, namely water, liquid sample, and air.

As used herein, the term "test chamber" is meant to refer broadly to any space adapted to receive a sample for testing, receive any other substances used in a test, and apparatus for conducting a test, including any flow channel for a fluid being tested or used for testing.

As used herein, the term "sensor" is meant to refer to any device for detecting and/or measuring a property of a person or of a substance regardless of how that property is detected or measured, including the absence of a target molecule or characteristic. Sensors may use a variety of technologies including, but not limited to, MOS (metal oxide semiconductor), CMOS (complementary metal oxide semiconductor), CCD (charge-coupled device), FET (field-effect transistors), nano-FET, MOSFET (metal oxide semiconductor field-effect transistors), spectrometers, volume measurement devices, weight sensors, temperature gauges, chromatographs, mass spectrometers, IR (infrared) detector, near IR detector, visible light detectors, and electrodes, microphones, load cells, pressure gauges, PPG (photoplethysmogram), thermometers (including IR and thermocouples), rheometers, durometers, pH detectors, scent detectors gas, and analyzers.

As used herein, the term "imaging sensor" is meant to refer to any device for detecting and/or measuring a property of a person or of a substance that relies on electromagnetic radiation of any wavelength (e.g., visible light, infrared light, xray) or sound waves (e.g., ultrasound) to view the surface or interior of a user or substance. The term "imaging sensor" does not require that an image or picture is created or stored even if the sensor is capable of creating an image.

As used herein, the term "data connection" and similar terms are meant to refer to any wired or wireless means of transmitting analog or digital data and a data connection may refer to a connection within a toilet system or with devices outside the toilet.

As used herein, the terms "biomarker" and "biological marker" are meant to refer to a measurable indicator of some biological state or condition, such as a normal biological processes, pathogenic processes, or pharmacologic responses to a therapeutic intervention. Some biomarkers are related to individual states or conditions. Other biomarkers are related to groups or classifications or states or conditions. For example, a biomarker may be symptomatic of a single disease or of a group of similar diseases that create the same biomarker.

As used herein, the prefix "nano" is meant to refer to something in size such that units are often converted to the nano-scale for ease before a value is provided. For example, the dimensions of a molecule may be given in nanometers rather than in meters.

As used herein, the term "jet" is intended to have a relatively broad meaning, referring to a stream of liquid flowing from some kind of nozzle, orifice, or other opening through which water is directed to create a stream of water with sufficient energy to flush or remove solid excreta and waste from the location, including stuck on solid excreta. While round openings are preferred, other shapes, such as narrow slits can also be used. The shape of the opening is not critical, so long as it creates the desired energy in the stream of water.

As used herein when referring to flush water, "energized" is meant to refer to an increase in the amount of pressure, velocity, and/or temperature of at least a potion of the flush water over that of the supply water and caused by a device which adds energy to the water. Such devices will generally be referred to by the term "energizer" and may include a pump which increases the pressure of the water, a pump which increases the velocity of the water, and a heater with increases the temperature of the water. Such a device generally requires a power source, such as electricity to power a motor, heater, or other device or such as moving water which spins a turbine. This is not meant to include a mere change of elevation of the water to convert its potential energy to kinetic energy.

Non-energized flush water has a maximum pressure of approximately the pressure of the water coming into the toilet from the water supply. In gravity tank toilets, the tank pressure generally drops to ambient pressure. For reference, gravity tank toilets generally require an incoming water pressures around 10-15 psi. Pressure assist tank and flushometer toilets generally require an incoming pressure of 25-40 psi or more. Standing water height of 2 feet—the approximate height above the p-trap of water in many toilet tanks—adds less than 1 psi to the total water pressure.

As used herein, "wastewater" is meant to refer to flush water, excrement, and other matter collected in the bowl or toilet which could lead to contamination of the toilet and/or excreta samples. Wastewater is generally removed therefrom prior to the next user using the toilet.

Exemplary Embodiments

The present disclosure relates to analytical toilets which have one or more analytical tool to perform excreta analysis. U.S. patent application Ser. No. 16/744,854 titled "Toilet equipped to Provide Fecal Analysis" filed 16 Jan. 2020, Ser. No. 16/812,019 titled "Toilet with Digitally Controlled Manifold to Distribute Fluids" filed 6 Mar. 2020, and Ser. No. 16/818,178 titled "Toilet with Sensor for Measuring Cleaning Consumable" filed 13 Mar. 2020 are pertinent to the present disclosure and are incorporated herein by reference in their entireties.

One benefit of the invention of the present disclosure is the improved ability to clean the toilet, which is particularly useful in analytical toilets where contaminants may undermine or compromise the analysis of a user's excreta. One goal of excreta analysis is to assess a person's current condition. If there are contaminating artifacts left over from a previous user or use of the toilet, those artifacts could skew the results of analysis performed on current excreta samples. Additionally, excreta includes organisms and other matter that can change over time once out of the body. For example, some studies indicate that room temperature storage of fecal samples affects the composition of their microbial communities, which may affect the % or number of biomarkers in the sample. Thus, even if the toilet has only been used by one user, fecal matter allowed to remain in the toilet from a previous use can skew the results of subsequent analysis.

Figure 1:
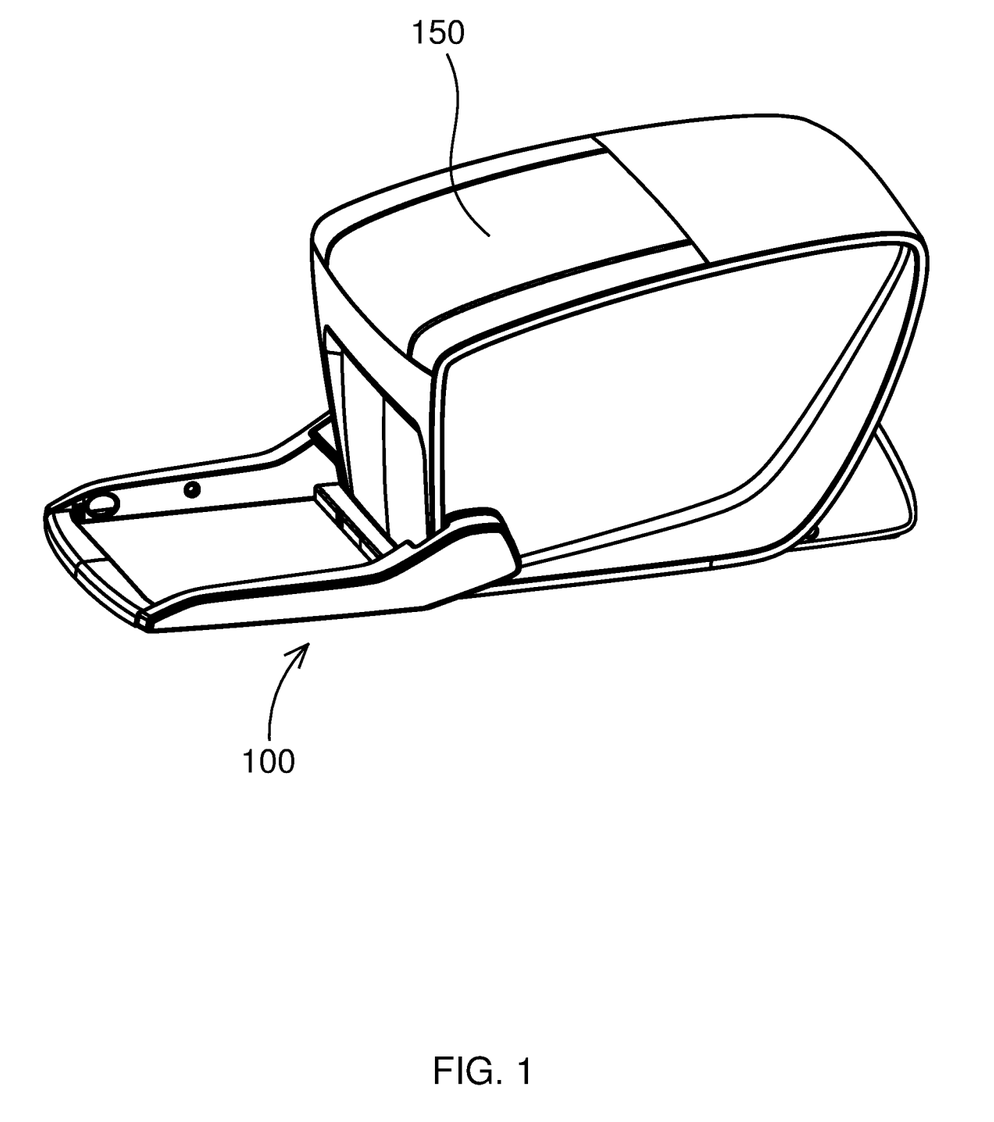
FIG. 1 is an isometric view of a first exemplary embodiment of a toilet according to the present disclosure.
Figure 2:
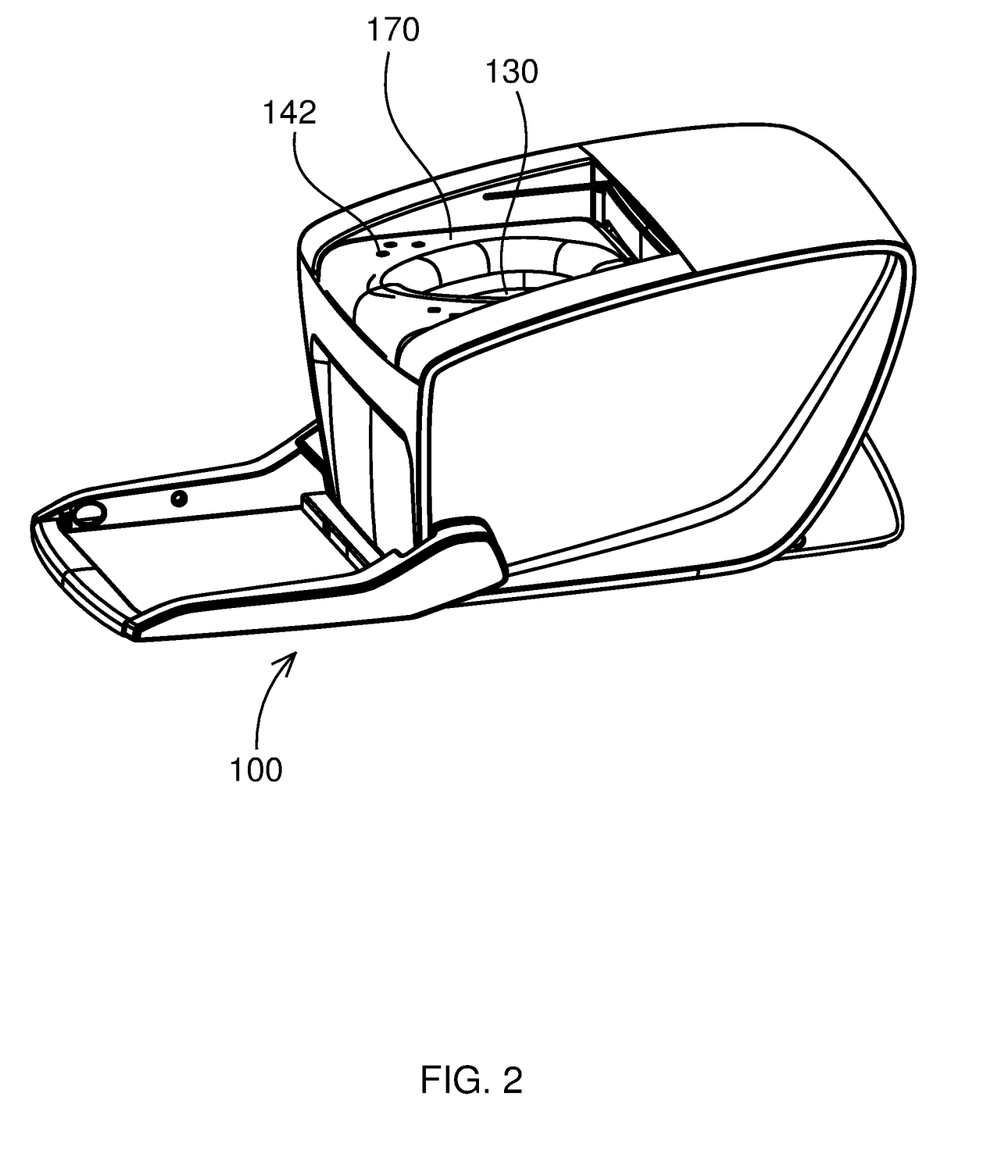
FIG. 2 is an isometric view of the toilet of FIG. 1.
Figure 3:
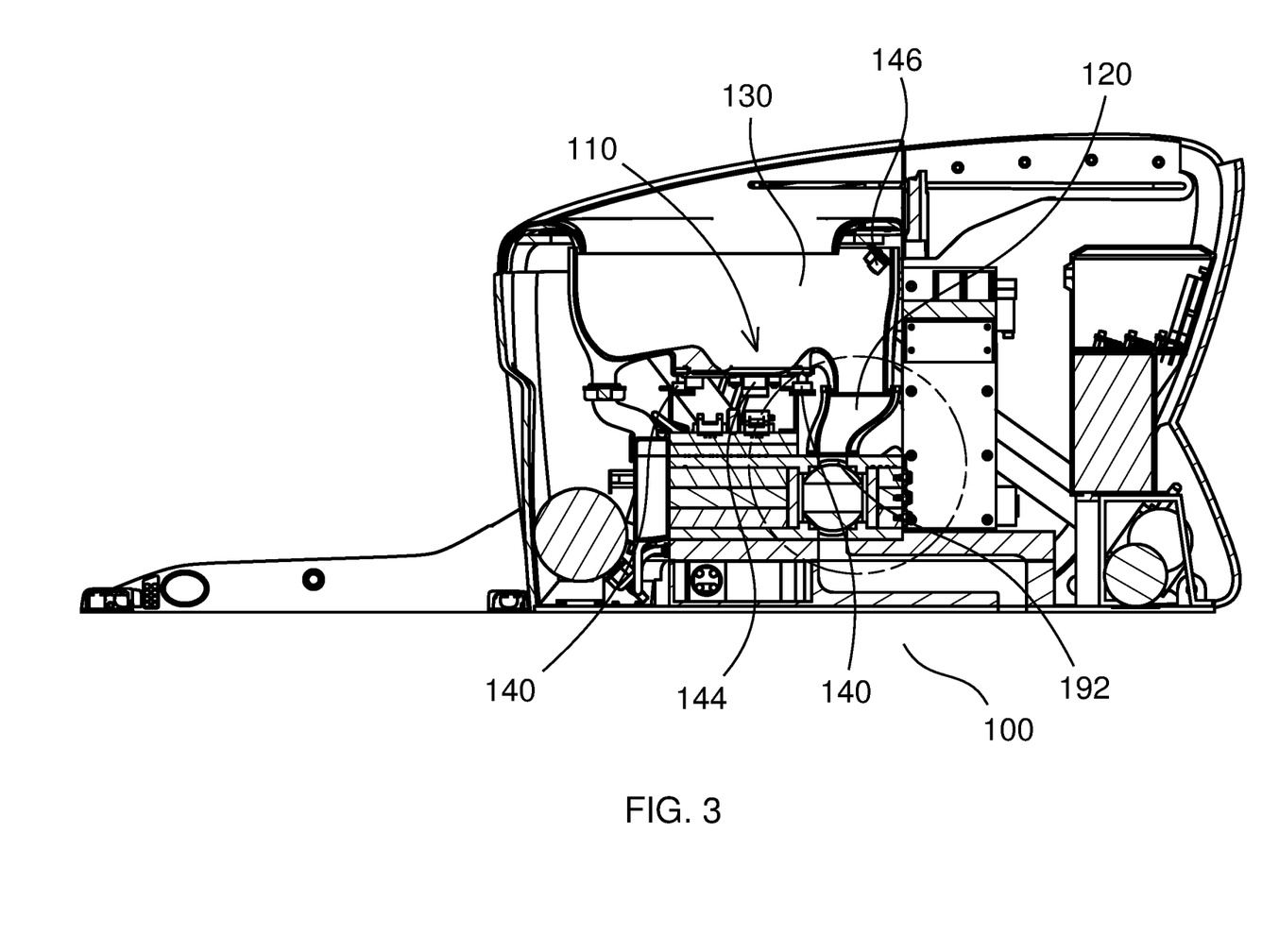
FIG. 3 is a cross section of the toilet of FIG. 1.

FIGS. 1-3 depict a toilet of one preferred embodiment. Toilet 100 includes seat 170 where a user may sit to deposit excreta into bowl 130. In front of toilet 100 is a foot platform where a user may stand and/or place their feet while using toilet 100. Toilet 100 includes various sensors, including photoplethysmogram ("PPG") sensors 142 in seat 170, and various other sensors and analytical devices.

In FIG. 1, lid 150 has been closed and cooperates with other components of toilet 100 to form an air seal within toilet 100, enclosing the space within toilet bowl 130, especially the parts adapted to receive feces or urine, from the environment around the toilet to facilitate cleaning and/or conducting analysis of the excreta. FIG. 2 shows toilet 100 with lid 150 open (lid not shown), exposing bowl 130 to the outside environment. FIG. 1 shows toilet 100 with lid 150 closed. Unlike traditional toilets, this preferred embodiment may seal the toilet, excreta processing areas, and/or excreta analysis areas from the outside environment to prevent exchange of air and/or fluid between them. In one preferred embodiment, there may be a seal between lid and the toilet such that there is no air gap. To ensure a sufficient seal, a seal or gasket may be placed between lid 150 and the portions of toilet 100 that mate to the lid, which may include seat 170 and the upper rim of bowl 130. Preferably the lid, the bowl, the seat, and/or other components of the toilet creating the air seal comprise a heat resistant material capable of repeated exposure to high temperatures associated with analysis incorporating heat treatment of the excreta, burning feces for analysis, or cleansing excreta from the toilet. In some embodiments there is a seal or gasket placed between the toilet seat and the upper rim of the toilet bowl to facilitate the air seal. Preferably, the seal or gasket is also made from a heat resistant material.

There is a shelf 110 upon which feces is deposited within toilet 100. This shelf may be integrated into the bowl or alternatively may be separate from the bowl. Additionally, bowl 130 is configured to separate the urine from the feces so they may be analyzed separately from each other. Alternatively, a design may be selected in which the bowl does not separate the urine from the feces. Preferably, shelf 110 is integrated into bowl 130, toilet 100 is configured with at least one sensor 140 to measure the weight of bowl 130, and the weight and/or mass of the feces is determined from the measurements of the weight of bowl 130. Preferably, sensor 140 can also measure the impact force of the feces being deposited onto shelf 110 and/or into bowl 130. Some ways of measuring of the weight of the bowl include a pressure sensor, a strain gauge, load cell, and a scale. Preferably, sensor 140 measures the weight of bowl 130. Additionally, shelf 110 is configured with an optical or spectral analysis sensor 144. Preferably, optical or spectral analysis sensor 144 is positioned below shelf 110 and shelf 110 is configured with a transparent or translucent portion through which sensor 144 analyzes the feces. It is also possible an optical or spectral analysis sensor is located to the side and/or above the shelf or at other analysis areas in the toilet. Preferably, the sensor for detecting a property of the feces is attached or connected to the toilet and/or its internal component by physically mounting and/or via an electronic data connection.

From shelf 110, excreta and other foreign waste can be moved to secondary processing area 120 or flushed out of the toilet. There are various methods of removing the waste from the bowl and shelf. These include a gravity flush as is common with many toilets, an assisted flush where the flush water is stored in the tank at the pressure of the supply water and has more energy during a flush, use of a pump in the toilet to increase the pressure, use of water from a hot water supply, and use of a heater to increase the temperature of the water. Some of these methods are depicted in FIGS. 4-9. U.S. patent application Ser. No. 16/744,854 referenced above has information regarding some additional methods from moving waste from the bowl and shelf and on what the toilet does with waste, particularly excreta.

Excreta and waste detector 146 includes a sensor which can be used to determine the location of excreta in the bowl. This can be used during the cleaning cycle of the toilet to determine whether there is any excreta or foreign matter in the bowl. Data from the sensor can also be used to determine the location of waste (i.e. excreta and foreign matter) that needs to be cleaned from the bowl. This location information can then be used to automatically turn on and/or aim one or more jet of water to remove the waste from the bowl. Data from the sensor can be sent to a controller or other processor and used in combination with various algorithms and rules to detect and/or determine the location of waste in the bowl and/or on the shelf. The controller may be in the toilet, a device nearby, or at another remote location. The sensor has a data connection to a controller. The sensor data may be sent as raw data or be processed first, such as with a digital or analog signal processor. The controller also has a data connection with a flush mechanism that controls the jet, such as a pump, valve, solenoid, manifold, or motor. Additionally, one embodiment may use the same or similar elements to detect the location of waste and clean waste from a user.

There are many ways to use the sensor data to detect and locate excreta and other waste in the toilet. The selection of which to use depend on many factors, including some which are outside the scope of the invention. Factors include designer preference, stakeholder preference, available resources, cost, ease of manufacture and maintenance, market conditions, and hardware selection. In one embodiment, the sensor detects visible or near visible light, the controller stores data of how the bowl and shelf look when clean, and the waste detection system identifies differences between the stored look and the current look to detect waste that needs to be removed. A variety of other sensor types could be used to accomplish a similar detection, including acoustic sensors and thermal sensors. Depending on the type of sensor being used, the detection system may include a feature to distinguish between liquid waste, which will likely be removed with a low energy flush, and solid or semi-solid waste, which may need to be removed with a jet.

Preferably, the jet of water is flush water. More preferably, the portion of the flush water used to create the jet has been energized prior to becoming the jet, such as by increasing the pressure or temperature of the water before flowing out the orifice to create the jet. Still more preferably, the energizing is by increasing the pressure of the flush water prior to use in the jet.

In one preferred embodiment, when feces is initially deposited into the toilet, the shelf supports non-diarrhetic feces (feces that essentially comprises non-watery stools) in a manner such that the feces is not submerged. In other words, there is minimal or no standing water in contact with the portion of the shelf where feces is deposited just prior to the feces being deposited. Preferably, the initial deposit of feces is into minimal or no standing water. This can create a greater tendency for feces to stick to the shelf.

Bowls and shelves for collecting feces, particularly those portions above standing water, frequently retain stuck waste after flushing with lower energy water to remove waste from the bowl. One or more concentrated jets on areas likely to have stuck waste would clean the area effectively. In one preferred embodiment, a jet is set to focus on a predetermined area that may need the assistance of a jet to remove sticking waste. In one preferred embodiment, a first jet is aimed at one location of the toilet where waste may stick, and a second jet is aimed at the same location. Alternatively, the second jet may be aimed at a second location where waste may stick.

In one preferred embodiment, one or more jet is aimed or selectively turned on to target one or more selected area with sticking waste after the toilet has been analyzed to determine where there is sticking waste. For example, in a preferred embodiment, a first jet is aimed at one location of the toilet where waste may stick, and a second jet is aimed at the same location. The first and second jets may be turned on at the same time or individually. Alternatively, the second jet may be aimed at a second location where waste may stick. Such analysis may be performed by an image sensor and algorithms trained to identify sticking waste locations. Alternatively, it may similarly be performed with an acoustic or other sensor instead of an image sensor. Such images may create privacy concern, so the image sensor can be implemented in a manner that uses the data without creating or storing images. Alternatively, a jet may be replaced with a laser which burns off sticking waste.

There are many ways to change the aim of a jet of water. Common methods include using a motor, gearing, or other driving mechanism to reposition the orifice forming and directing the jet. Another method includes varying the pressure of the water feeding the jet, changing the way the water leaves the orifice and forms the jet. Another method includes aiming multiple primary jets to form a combined jet and then selectively varying the pressure to one or more of the primary jets to adjust the aim of the combined jet. As noted generally elsewhere in the disclosure, the selection of which method to use depends on many factors.

Figure 4:
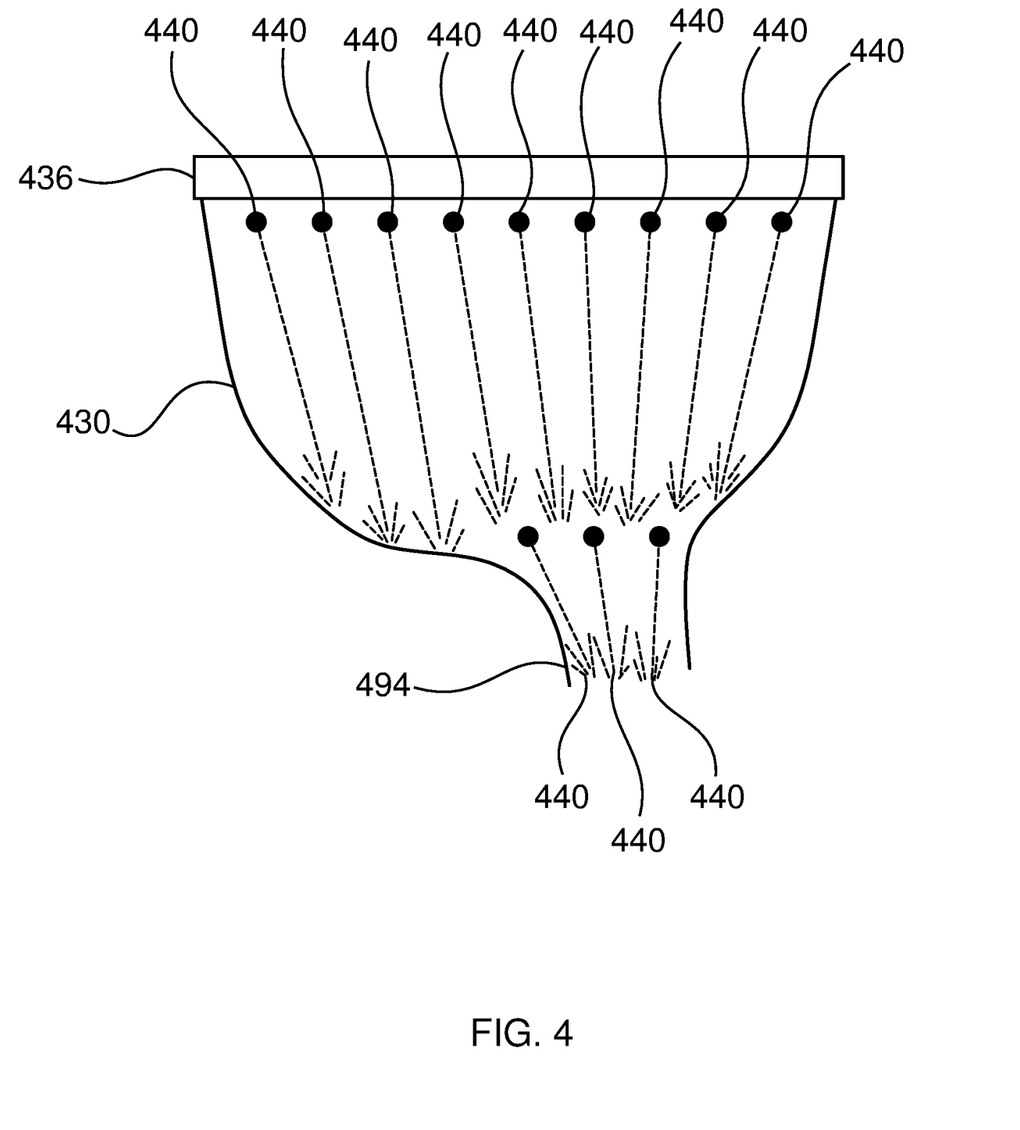
FIG. 4 is a cross section view of a portion of a bowl of a second exemplary embodiment of a toilet according to the present disclosure.

In one preferred embodiment and as shown in FIG. 4, there are multiple orifices and jets 440 which target various predetermined areas of the shelf and bowl 430 as depicted, some of these orifices are located just below rim 436 and direct the jet downward. Waste is collected by area 494, which may lead to a secondary processing location or to a waste receptacle such as a sewer, septic system, or black water storage tank. Each orifice and jet 440 may be activated individually or as a group with some or all of the other jets 440. This may be passively part of the design or actively controlled through electronics, valving, geometry, and/or other factors elements, especially when integrated with a system that detects and locates sticking waste that needs to be removed from the bowl and/or shelf. In one embodiment, the aim of the jets is relatively fixed, perhaps being slightly controllable by varying the flush water pressure. In an alternative embodiment, the aim of at least one jet is adjustable. In yet another alternative embodiment, two or more primary jets are aimed to intersect and create a combined jet. The combined jet may be aimed by varying the pressure of one of the initial jets, thereby increasing the area targetable by the combined jet over that of each primary jet.

Bidets are primarily used to wash and clean the genitalia, perineum, inner buttocks, and anus. Many bidets come in the form of a freestanding plumbing fixture adjacent to a toilet. Some toilets include an integrated bidet which may be built-in or an add-on. Integrated bidets generally have an orifice which issues a jet to clean the user and generally connect to the existing water supply of a toilet, such as by the addition of a threaded tee pipe adapter which thus requires no soldering or other plumbing work. Integrated bidets may include additional features, such as a heater to warm the water prior to it being used to cleaning the user, oscillation of the direction of the jet, reduction of the water pressure, and the ability to extend and retract the bidet (especially helpful in keeping the bidet out of the way while the user is depositing excreta into the toilet). Electronic integrated bidets also typically require a GFCI protected grounded electrical outlet.

In some preferred embodiments, an integrated bidet (or similar non-bidet device) is included in or added to a toilet and adapted to clean excreta and other waste from the bowl. There are many ways to increase the area of the toilet the bidet may clean. For example, the bidet may be adapted to extend and retract. It may also be adapted to rotate around the axis along which it extents and retracts. Additionally, the orifice may be on a nozzle which can angle and/or the water pressure feeding the orifice may be varied to change the angle of the jet. The bidet may use the same orifice to clean both the user and the toilet; this may create a safety or splatter concern, especially if the jet can be energized, so the use of energized flush water may have a safety or lock out feature that controls when the energized water can be used. Alternatively, the bidet may have separate orifices for cleaning the user and for cleaning the toilet. The bidet may use the same water to clean a user and clean the toilet or it may use one supply of water to clean the user and a different supply to clean the toilet. Alternatively, the bidet may use a combination of energized and non-energized water to clean the user and/or toilet. As noted by the disclosure, the energizer may increase the pressure and/or temperature of the water well above values which a user may safely be exposed to. In one preferred embodiment, the pressure and temperature of the water used to clean the user is limited, such as by limiting to wall pressure and wall temperature, limiting pressure to a value under 100 psi, and/or limiting temperature to a value under 111° F.

Figure 5:
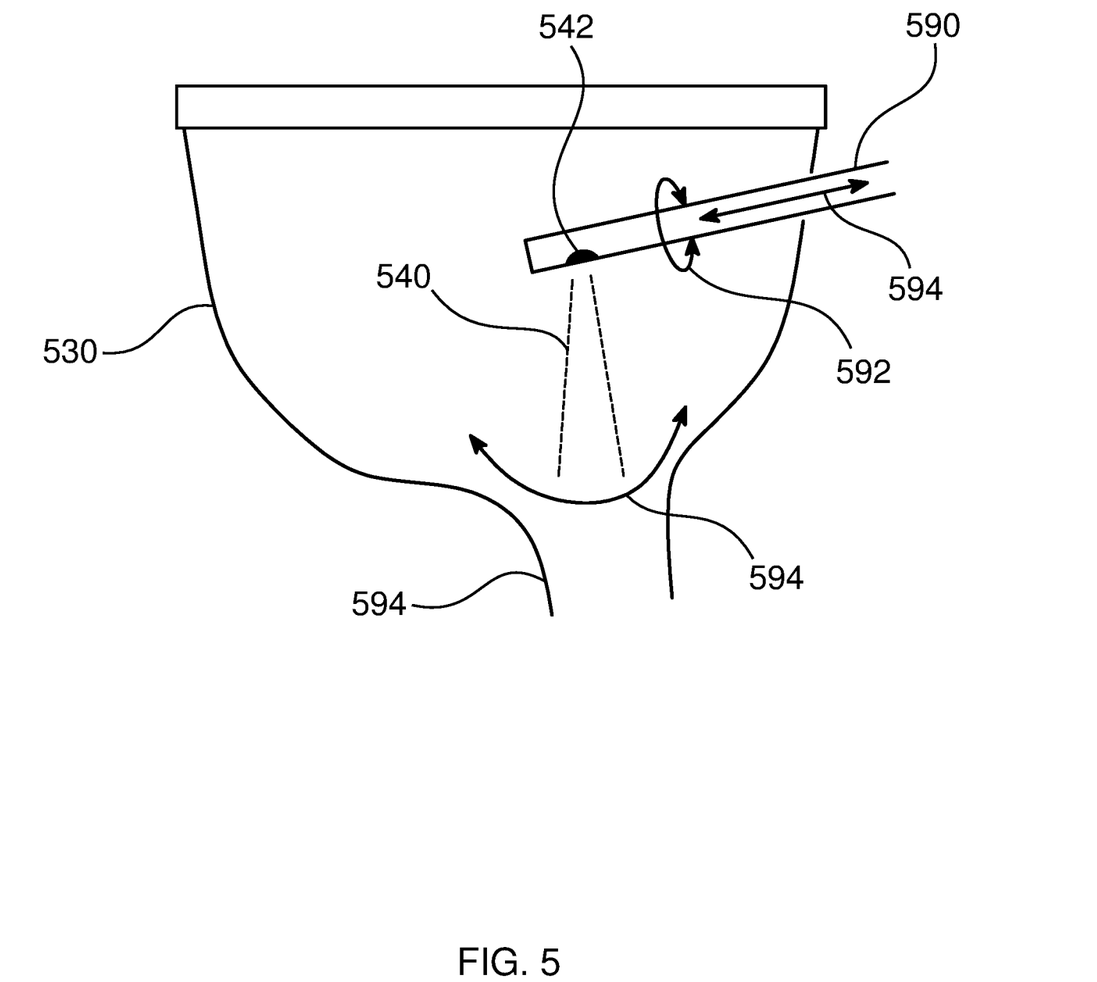
FIG. 5 is a cross section view of a portion of a bowl of a third exemplary embodiment of a toilet according to the present disclosure.

In an embodiment with elements represented in FIG. 5, jet 540 comes from orifice 542 on toilet cleaning bidet 590. As indicated by arrow 592, bidet 590 can rotate along it's longitudinal axis relative to bowl 530, allowing jet 540 to sweep across and/or target additional portions of bowl 530; the longitudinal axis is or is approximately the axis along which bidet 590 extends and retracts. Additionally, as indicated by arrow 594, bidet 594 may extend farther into or retreat from bowl 530, allowing jet 540 to be directed at different portions of the toilet. Orifice 542 may be on or part of a mechanism which can be directed at different angles, such as a nozzle, allowing jet 540 to sweep across and/or target additional portions of bowl 530, including changing angle along a plane intersecting the orifice and the central axis of the bidet as well as a plane bisecting the central axis of the bidet. The locations jet 540 is aimed at may be predetermined or may be determined based on the results from a waste detecting and locating system.

The size of the jet can vary, depending on the number of streams and the pressure. In one preferred embodiment, the toilet includes 4 or more jets. Alternatively, one well-placed and well directed jet may be preferable in some embodiments.

The jet array can have a single or multiple entries at a single or varying areas in the bowl, rim, flush tube(s), or P-trap. These holes can have circular exits or be oblong or slits to enhance the cleaning and/or syphon-initiation.

Figure 6:
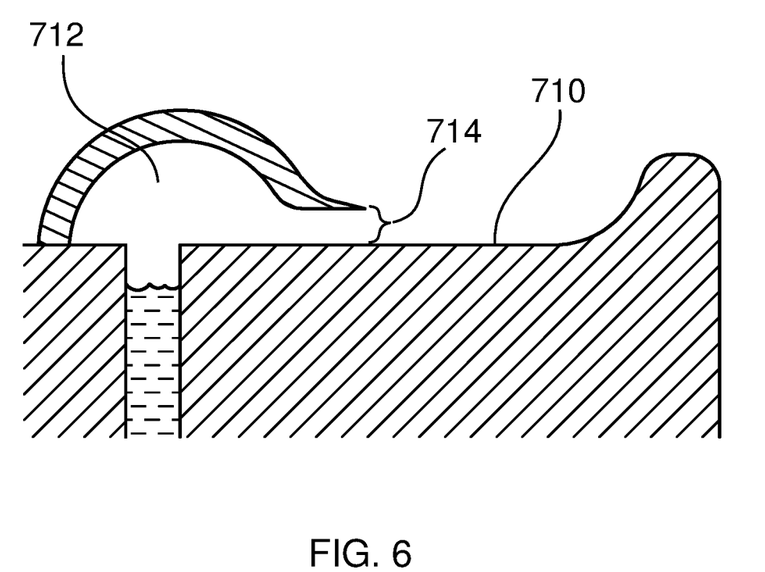
FIG. 6 is a cross section view of a first exemplary embodiment of a shelf in a toilet according to the present disclosure.
Figure 7:
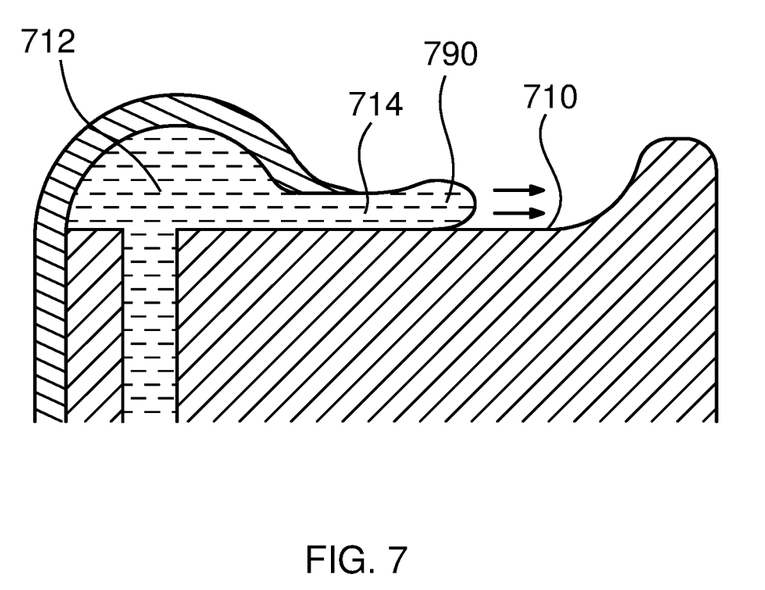
FIG. 7 is a cross section view of the shelf of FIG. 6.

In one preferred embodiment shown in FIGS. 6-7, a jet of water may be supplied to shelf 710 via wave 790 of water. More preferably, flush water enters cavity 712 proximate to the shelf, wherein the cavity has an outlet 714 directing wave 790 at shelf 710 to clean the shelf of feces. Preferably, the opening of outlet 714 is approximately ⅛"-¼" high and the width of the shelf. In one preferred embodiment, cleaning and/or sterilizing agents are added to the water to aid in cleaning and/or sterilizing the shelf.

Figure 8A:
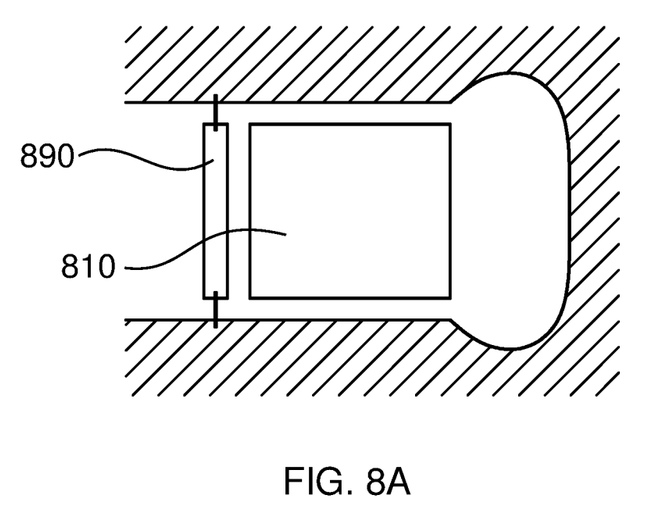
FIG. 8A is a top view of a second exemplary embodiment of a shelf in a toilet according to the present disclosure.
Figure 8B:
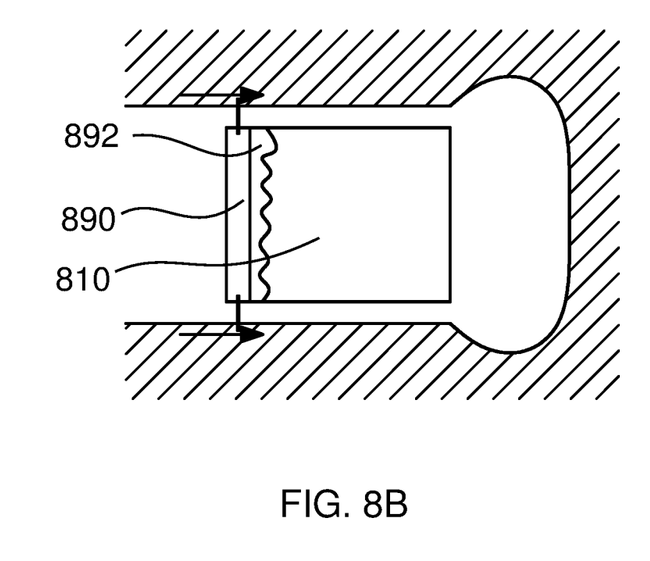
FIG. 8B is a top view of the shelf of FIG. 8A.
Figure 8C:
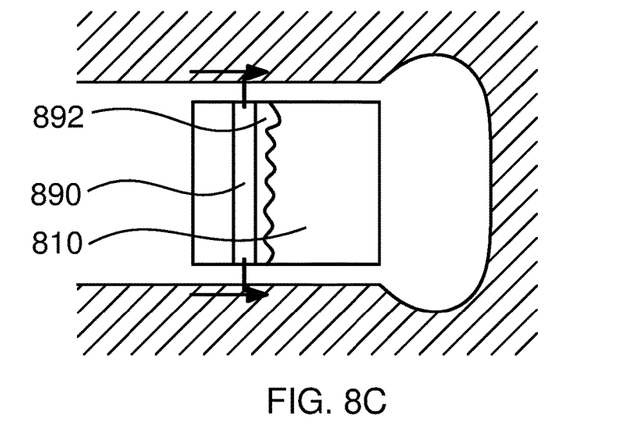
FIG. 8C is a top view of the shelf of FIG. 8A.
Figure 8D:
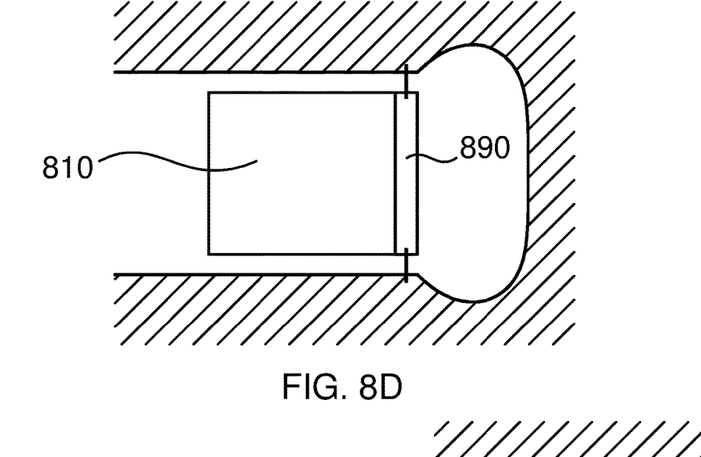
FIG. 8D is a top view of the shelf of FIG. 8A.
Figure 8E:
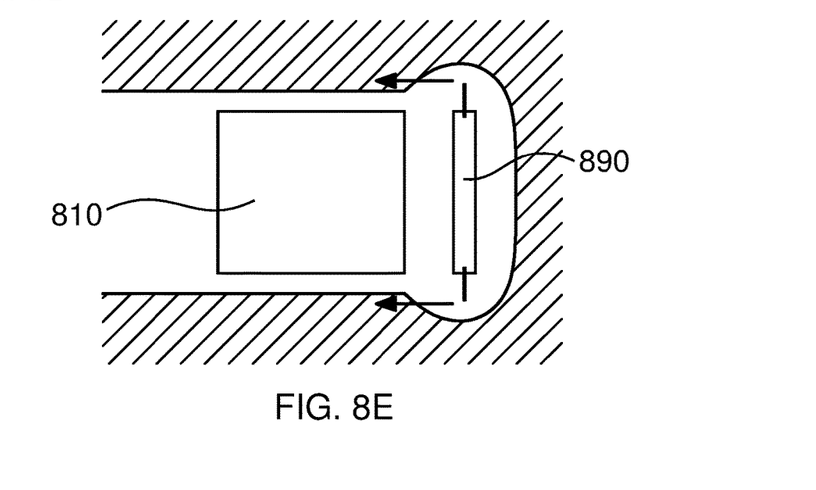
FIG. 8E is a top view of the shelf of FIG. 8A.
Figure 9A:
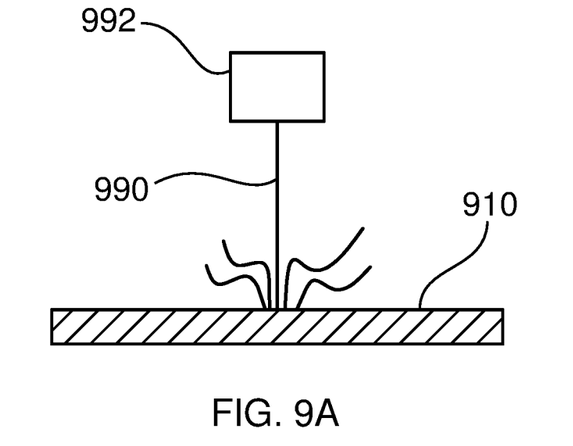
FIG. 9A is a cross section view of an exemplary embodiment of a water jet according to the present disclosure.
Figure 9B:
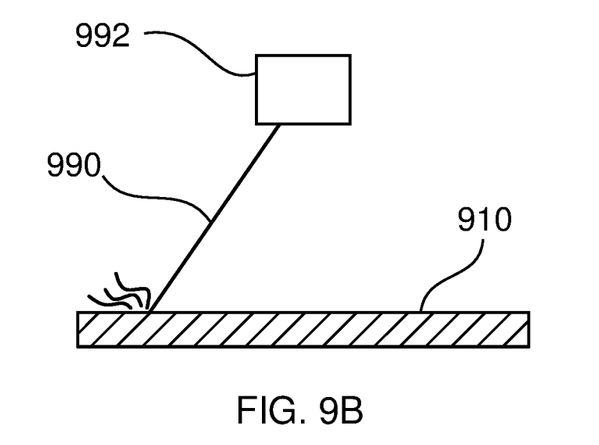
FIG. 9B is a cross section view of the water jet of FIG. 9A.
Figure 9C:
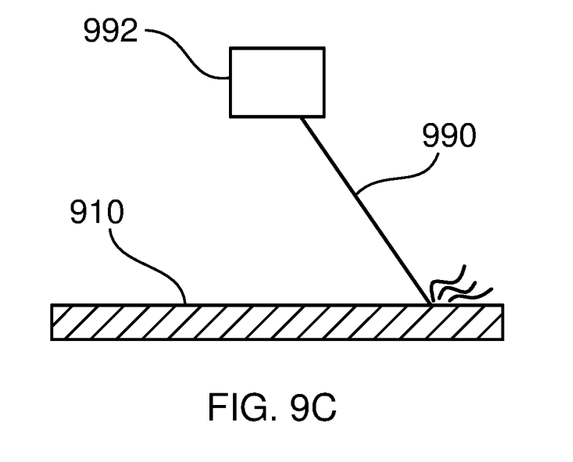
FIG. 9C is another cross section view of the water jet of FIG. 9A.

In an alternative embodiment, there is a squeegee that wipes the shelf to remove the feces. Alternatively, one or more jet of water or a water blade is sprayed onto the shelf to remove the feces from and/or sterilize the shelf. In an embodiment depicted in FIGS. 8A, 8B, 8C, 8D, and 8E, squeegee 890 is configured so one or more water jet or a water blade sprays shelf 810 as squeegee 890 traverses shelf 810, creating water spray 892. The squeegee 890 may only travel the distance of the shelf 810 as depicted in FIGS. 8B, 8C, and 8D, or the squeegee 890 may also travel beyond a side of shelf 810 as depicted in FIG. 8a or 8e. As depicted in FIGS. 9A, 9B, and 9C, nozzle 992 supplies jet 990 and is fixed in location within the toilet. Nozzle 992 is configured to be able to change the direction of jet 990 to target specific spots on the shelf. Accompanying a directable jet would be a system for controlling the direction and a system that determines where the jet needs to be directed. Again, the water in a jet may have additives for cleaning and/or sterilizing the shelf and/or other elements of the toilet.

In many cases, the water readily available for use in a toilet will be tap water. The temperature of available tap water varies greatly between 32° F. to 150° F. or higher and depends on factors such as time of year, whether the pipes supplying the water had a significant run underground, and if the water went through a water heater. Generally, tap water for toilets comes from underground pipes (which in the United States often have a temperature around 40 to 60° F.), may be temporarily stored in a reservoir within a building, and bypasses any water heaters that supply hot water. Tap water pressure can vary from ambient up to 150 psi (gauge) or higher and depends on factors such as the pressure in the supply line or elevation of reservoirs, pressure regulators, head loss, and whether other valves in the system are open. City supplied residential water pressure is often around 40-70 psi and, when installed, pressure regulators often keep the incoming water at a maximum around 50 psi. In taller buildings, the water pressure to the building is insufficient to provide water at sufficient pressures where the water is needed so such buildings may use pressure increasing systems. Additionally, tap water has a varying molecular composition since water typically has naturally occurring trace minerals and various additives to control the quality of the water.

The characteristics of tap water supplied to the toilet may or may not be adequate. As such, the toilet may be configured to change the water in a variety of ways, including heating the water, cooling the water, purifying the water, electrolyzing the water, deionizing the water, adding additives to the water, increasing the pressure, and decreasing the pressure. Additionally, such changes could be performed before the water enters the toilet.

Cleaning of sticking waste from the bowl and/or shelf may come in a variety of stages, including an initial water flush to remove a significant portion of waste, use of energized flush water to unstick and/or remove waste, an analysis to determine if and where sticking waste is, collection of waste into a lower portion of the bowl or toilet, and a secondary or final flush to remove all of the remaining waste. In one preferred embodiment, there is an initial flush, use of one or more targeted energized jets, collection of all waste, and a final flush to remove all waste from the bowl and shelf.

As discussed in U.S. patent application Ser. No. 16/812,019, various exemplary embodiments of the analytical toilet provide a fluid processing manifold that collects and routes samples from the toilet bowl to various scientific test devices and waste handling portals throughout the toilet. Cleaning methods and elements similar to the above may be used to clean waste from the fluid processing manifold. Additionally, the fluid processing manifold is likely to have channels, piping, or other constricted portions that need cleaning. In these cases, the jet of water may be internal to confined spaces such as these.

In one preferred embodiment, the toilet includes a cleaning mechanism for the manifold. More preferably, the cleaning mechanism includes flushing the fluid pathways of the manifold with a fluid to remove waste and/or sterilize them. There are a number of possible options for the fluid, the selection of which depends on a number of factors, some of which are outside the scope of the invention. Factors include what analysis has been selected for use; chemicals introduced to the system; regulations for handling of excreta, chemicals, and waste; design preferences; material availability; and cost. For example, the fluid may be flush water.

There are many ways the flush water could be specially prepared to clean the toilet, including pressurizing by a pressurizer, heating by a heater, adding a cleaning agent, or adding a sterilizing agent. Each provides its own benefits. For example, increased pressure increases the flow rate of the flush water and/or jet, thus increasing the amount of force being applied to sticking waste. Increased temperature can help break down waste, loosening any hold it may have on the toilet surface. Cleaning additives are selected and/or designed to improve the ability of the flush water to remove waste from the toilet and/or sterilize the toilet. Each of these elements can contribute to a general desire for cleanliness of the toilet, including visual appeal and preventing undesirable odors from developing. Additionally, each of these elements can serve to ensure the integrity of the analytical tests. While some analytical equipment may have sufficient automatic cleaning mechanisms, toilets generally do not clean sufficiently to ensure the integrity of many analyses, especially those that detect through surfaces that may retain waste or those that detect analytes or biological markers. One drawback of many typical toilets is that a person may need to manually clean the toilet bowl and other relevant parts between uses to ensure the integrity of analysis results.

This manual cleaning may be at least partially removed through pretreating flush water in the water tank, such as with a tablet of chemical cleaner that slowly dissolves into the flush water over the course of many flushes. One advantage of the current disclosure is that it can mitigate or even remove the need to manually clean the toilet under normal use conditions.

In one preferred embodiment, the energizer includes a pump that increases the pressure of the flush water. More preferably, the pump is an in-line pump that increases the pressure while the flush water is traveling to a jet nozzle, orifice, or other opening or to a manifold that then leads to a jet. One such pump is the PumpTec Model 112T, which is a 120 volt plunger pump/motor unit with ¼" FPT inlet and outlet connections and is rated to 250 psi and 140° F. Alternatively, the pump increases the pressure of flush water stored in a storage container. This may be accomplished through the use of a hydraulic pump that directly acts on the flush water. It may also be accomplished through the use of a pneumatic pump that increases the pressure of air (or another gas) and the air acts to increase the pressure on the water.

Energized flush water with increased pressure has a pressure that is preferably at least 80 psi, more preferably 100 psi, and most preferably at least 120 psi. Higher pressures might also be used, for example, pressures above 150 psi or about 180 psi.

Hot water cleans surfaces quicker than cold water. It melts fats and greases away more effectively and the molecules in the water move more quickly, adding more energy to waste it encounters. By supplying hot water to the bowl, possibly in an intelligent directed manner, sticking waste may be more quickly cleaned. By selectively using heated water, especially selecting to use it on sticking waste, one is able to have the benefits of cleaning with hot water while not wasting it to clean waste that could easily be removed without hot water. The hot water could be a substage of a general flush and/or could be used as part of a targeted energized cleaning. When used in an embodiment that can also increase the pressure of the flush water, adding pressure and adding heat may be used together or separately.

In one preferred embodiment, the hot water is at least 110° F., more preferably over 140° F., and most preferably over 150° F. Higher temperatures may also be used, for example, temperatures above 170° F. and up to the boiling point. Additionally, the flush water can be heated past the boiling point to create steam to be used for cleaning.

In one preferred embodiment, the energizer includes a heater that increases the temperature of the flush water. This heater may be an in-line heater which heats the water while it is in transit within the toilet. Alternatively, the heater may heat a supply of flush water stored within the toilet. In one preferred embodiment, the heater is located in the lower portion of the fluid processing manifold and heats flush water in a chamber within the fluid processing manifold. In an alternative embodiment, the heater heats flush water into steam and the steam is used to clean various parts of the toilet.

One potential source of hot water is a hot water tap that comes from a building's hot water heater. This provides the benefit of hot water without the need for a heater in the toilet. One drawback of this option is that the hot water has to travel a longer distance before being used in the toilet for cleaning. This could cause the water to cool off during travel. Additionally, hot water may be stored in piping between the water heater and the toilet long enough for the water to cool. Thus, hot water may not be immediately available to the toilet from the hot water tap. One embodiment of the toilet includes a connection to a hot water tap, a temperature sensor to detect the temperature of the water from the hot water tap, and a mechanism to dump water from the hot water tap such as may be desired if the water is not hot enough.

With higher pressure and/or temperatures, safety becomes a greater concern. Both higher pressure and temperature can directly cause harm to people, including through damage to the skin if the water contacts the skin. For example, a force applied with approximately 100 psi can break the human skin. The minimum temperature that can burn the skin is approximately 111° F. for exposures over 6 hours; the rate of burn approximately doubles for each 2° F. up to 140° F.; 160° F. can cause burns in under one second. In one preferred embodiment, a safety feature may be used to ensure high pressure or temperature water does not contact the user.

Additionally, the expected pressures and temperatures need to be considered in design and material selection so as to ensure the structures, hardware, and other components can function safely and as intended. For example, the Model 112T is rated for 250 psi and 140° F. The pump may be considered for an embodiment where tank water or tap water is being pressurized to 180 psi. But, if the water is being heated above 140° F. before being pumped, a different pump may need to be considered. Additionally, pipes are rated for different pressures and temperatures. Selecting a pipe that is not intended for the desired pressures and/or temperatures could cause the pipe to catastrophically fail, potentially damaging nearby equipment and/or people through exposure to the water or shrapnel.

In one preferred embodiment, forceful water jets can induce rapid water movement that can aid in quickly starting a syphon to flush the toilet with little additional water. High impact from pressurized water can quickly move away waste that is stuck to the toilet bowl.

In one preferred embodiment, the flush includes multiple stages. These stages may include a lower pressure rinse (such as from the top of the bowl down), targeted energized cleaning of the bowl and other surfaces with or expected to have sticking waste, and a flush to remove the waste from the bowl and/or toilet. These stages can occur in any order and may happen multiple times. For example, a low pressure rinse may be used to clear much of the excreta from the bowl. After which, a jet of energized flush water may target one or more surfaces where there is or is a high probability of being sticking waste, such as a shelf to receive feces that's above the standing water line in the bowl or a portion of the bowl below the standing water line where the feces typically gets stuck. After which, the wastewater that has collected may be flushed from the bowl out of the toilet or into another area of the toilet for additional processing. Alternatively, energized flush water jets may be sprayed from the top of the bowl downward to clean any sticking waste into the wastewater. These jets may turn on simultaneously, individually, or in groups. They may be turned on in a predetermined pattern or sequence or they may be selectively turned on following an analysis which determines where sticking waste is located.

There are a wide variety of acceptable choices for the geometry, materials of construction, manufacturing processes, and other elements of the design, manufacture, and implementation of the invention, including the electrical hardware and software. The selection of these various elements depends on a number of factors, including costs, supply chain, availability of labor and materials, design forces and safety factors, designer and stakeholder preference, local laws and regulations, and other market conditions. For example, there are a wide variety of potential materials that the various elements of the invention could be made from. Regarding those that take weight and other forces, many materials can be designed to bear the forces associated with a user's weight and potential tremors. Therefore, numerous other factors outside the scope of the invention play into the selected design, such as space, weight, production and installation costs, and maintenance requirements.

One common material of construction for toilets is porcelain. Other common materials of construction using for toilets components includes metal and plastic. Additionally, fluid pathways such as pipes are often built into the porcelain, constructed of metal, or constructed from plastic.

All patents, published patent applications, and other publications referred to herein are incorporated herein by reference. The invention has been described with reference to various specific and preferred embodiments and techniques. Nevertheless, it is understood that many variations and modifications may be made while remaining within the spirit and scope of the invention.

What is claimed is:

1. An analytical toilet comprising:
   a bowl for receiving excreta from a user;
   at least one analytical device by which a sample of excreta is analyzed, the at least one analytical device comprising a sensor used to detect the location of waste in the bowl;
   a supply of flush water to be used to remove waste from a surface the of the toilet;
   an energizer to add energy to at least a portion of the flush water to create energized flush water prior to its use in removing waste; and
   an orifice for directing a first jet of the energized flush water at the waste on the surface of the toilet;
   wherein the jet of energized flush water is selectively activated or selectively aimed to remove the waste based on the detected location of waste.

2. The analytical toilet of claim 1, wherein the energizer increases the pressure of the flush water.

3. The analytical toilet of claim 1, wherein the energizer increases the temperature of the flush water.

4. The analytical toilet of claim 1, wherein the bowl comprises a shelf for receiving feces and the first jet is directed toward the shelf.

5. The analytical toilet of claim 1, wherein the energizer comprises a pump.

6. The analytical toilet of claim 5, wherein the energizer comprises a pneumatic pump which pressurizes air and wherein the pressurized air is used to pressurize the flush water.

7. The analytical toilet of claim 1, wherein the energizer comprises a storage chamber for storing pressurized water before use.

8. The analytical toilet of claim 1, wherein the orifice is located on a bidet.

9. The analytical toilet of claim 8, wherein the orifice is in the form of a nozzle and wherein the nozzle can be directed at different angles.

10. The analytical toilet of claim 8, wherein the bidet is adapted to rotate about a longitudinal axis to change the location at which the first jet is directed.

11. The analytical toilet of claim 1, further comprising a lid which closes to prevent splatter from the first jet leaving the toilet.

12. The analytical toilet of claim 11, wherein the lid automatically closes before the first jet turns on.

13. The analytical toilet of claim 1, further comprising a second orifice for directing a second jet of flush water at the waste.

14. The analytical toilet of claim 13, wherein the first jet and the second jet are directed at different locations.

15. The analytical toilet of claim 13, wherein the first jet and the second jet are directed at the same location and cooperate to remove the waste.

16. The analytical toilet of claim 13, further comprising a valve for selecting which of the first jet or second jet is turned on.

17. The analytical toilet of claim 1, wherein the at least one analytical device comprises at least one sensor for performing analysis of excreta samples.

18. The analytical toilet of claim 1, wherein the orifice can be repositioned to direct the jet at multiple portions of the toilet.

19. The analytical toilet of claim 1, wherein the flush water is divided between the at least a portion of the flush water and the remainder of the flush water, and wherein the remainder of the flush water is not energized before being used to remove waste.

* * * * *